(12) United States Patent
Petrella

(10) Patent No.: US 9,072,779 B2
(45) Date of Patent: Jul. 7, 2015

(54) TREATMENT OF SOFT TISSUE INJURY USING HYALURONIC ACID AND BOTULINUM TOXIN

(76) Inventor: Robert John Petrella, London (CA)

( * ) Notice: Subject to any disclaimer, the term of this patent is extended or adjusted under 35 U.S.C. 154(b) by 882 days.

(21) Appl. No.: 12/683,351

(22) Filed: Jan. 6, 2010

(65) Prior Publication Data

US 2010/0172940 A1    Jul. 8, 2010

Related U.S. Application Data

(60) Provisional application No. 61/142,941, filed on Jan. 7, 2009.

(51) Int. Cl.
| | |
|---|---|
| A61K 38/48 | (2006.01) |
| A61K 39/08 | (2006.01) |
| A61K 31/728 | (2006.01) |
| A61K 9/00 | (2006.01) |
| A61K 45/06 | (2006.01) |

(52) U.S. Cl.
CPC ............... *A61K 45/06* (2013.01); *A61K 31/728* (2013.01); *A61K 38/4893* (2013.01)

(58) Field of Classification Search
None
See application file for complete search history.

(56) References Cited

U.S. PATENT DOCUMENTS

2004/0028704 A1 * 2/2004 Pappagallo et al. ........ 424/239.1

FOREIGN PATENT DOCUMENTS

| CA | 2578250 A1 | 2/2006 |
|---|---|---|
| EP | 1677806 B1 | 11/2008 |
| WO | WO 2004/060384 * | 7/2004 |
| WO | WO 2004/060384 A2 * | 7/2004 |
| WO | WO 2005/032562 A1 | 4/2005 |
| WO | 2006/084353 A1 | 8/2006 |
| WO | 2006/116302 A2 | 11/2006 |

OTHER PUBLICATIONS

Petrella et al, Sports MEd. Arthrosc. Rehabil. Ther. Technol., Feb. 2, 2010; 2:4, 6 pages.*
Paoloni et al, MJA 2005, 183/7:384-388.*
Mosiello, et al., "A Minimally Invasive Approach in the Treatment of Vesicoureteral Reflux in Neurogenic Bladder in Children", European Urology, vol. 55, No. 1, Jul. 18, 2008, pp. 254-256.
Placzek, et al., "Treatment of chronic radial epicondylitits with botulinum toxin A: A double-blind, placebo-controlled, randomized multicenter study", Journal of Bone and Joint Surgery—Series A 200702 US, vol. 89, No. 2, Feb. 2007, pp. 255-260.
Supplementary European Search Report for European Application No. 10 72 9069 dated Nov. 22, 2012.
Balazs, E. A., et al., "Viscosupplementation: A new concept in the treatment of osteoarthritis," The Journal of Rheumatology, 1993, pp. 3-9, vol. 20, supplement 39.
Hayton, M.J. et al., "Botulinum toxin injection in the treatment of tennis elbow," The Journal of Bone and Joint Surgery, Mar. 2005, pp. 503-507, vol. 87-A, No. 3.
Maheu, E. et al., "A hyaluronan preparation (500-730 KDA) in the treatment of osteoarthritis: A review of clinical trials with hyalgan®," International Journal of Clinical Practice, Dec. 2002, pp. 804-813, vol. 56, No. 10.
Matsuno, H. et al., "Biochemical effect of intra-articular injections of high molecular weight hyaluronate in rheumatoid arthritis patients," Inflammation Research, 1999, pp. 154-159, vol. 48, Birkhäuser Verlag, Basel, Switzerland.
Petrella, Robert J., et al., "Periarticular Hyaluronic Acid in Acute Ankle Sprain," Clinical Journal of Sport Medicine, Jul. 2007, pp. 251-257, vol. 17, No. 4, Lippincott Williams & Wilkins.
Wong, S. M. et al., "Treatment of lateral epicondylitis with botulinum toxin," Annals of Internal Medicine, Dec. 6, 2005, pp. 793-797, vol. 143, No. 11, American College of Physicians.
Zattoni, G. et al., "Efficacy and tolerability of hyaluronic acid in acute knee injury: A controlled clinical study," Reproduction, representation et diffusion interdites, 1992.
International Search Report dated Apr. 6, 2010, for International Application No. PCT/CA2010/000008.
Speed, C.A., Injection therapies for soft-tissue lesions, Best Practice & Research Clinical Rheumatology, Apr. 2007, vol. 21, Issue 2, pp. 333-347.
Written Opinion dated Apr. 6, 2010, for International Application No. PCT/CA2010/000008.
Zattoni, G. et al., Efficacy and tolerability of hyaluronic acid in acute knee injury: a controlled clinical study, European Journal of Rheumatology and Inflammation, 1995, vol. 15, Issue 1, pp. 63-69.

* cited by examiner

*Primary Examiner* — Nita M Minnifield
(74) *Attorney, Agent, or Firm* — Knobbe, Martens, Olson & Bear, LLP

(57) ABSTRACT

There is provided a method for supporting soft tissue in a mammal. The method may in aspects treat acutely or chronically injured soft tissue in an animal or human, the method comprising administering a therapeutically effective amount of HA and botulinum toxin in combination around the injured soft tissue. The method is useful for the treatment of sprain and strain in an animal such as a human.

21 Claims, 2 Drawing Sheets

TREATMENT OF SOFT TISSUE INJURY USING HYALURONIC ACID AND BOTULINUM TOXIN

RELATED APPLICATIONS

This application claims the benefit of U.S. Provisional Application No. 61/142,941 filed Jan. 7, 2009 which is incorporated herein in its entirety by this reference.

FIELD OF THE INVENTION

The present invention relates to the treatment of soft tissue, and more particularly to the combined use of hyaluronic acid and botulinum toxin in the treatment of soft tissue injury in animals and humans.

BACKGROUND

Every year, millions of people seek medical treatments for acute or overuse injuries of soft tissue, for example, injury to ligaments (sprain), or musculo-tendinous structures (strain).

In the example of sprain, soft tissue sprain injury can vary from first degree (slight ligamentous tear) to second degree (greater tearing with blood clot formation and moderate functional impairment) to third degree (total separation of the ligament associated with loss of function and mechanical stability). Symptoms include pain, heat, redness, swelling and functional loss. Therapies for sprain are directed at decreasing inflammation and pain. Treatment of mild to moderate sprains (first and second degrees) is usually done at home with rest, ice, compression and elevation (the so-called RICE treatment, rest-ice-compression-elevation), the use of nonsteroidal anti-inflammatory drugs (NSAIDs) that include aspirin, ibuprofen and naproxen, or immobilization with various devices including braces or plaster casts. More severe injury may require splinting, casting, or even surgical stabilization.

Soft tissue injury can also include strains that result from a traumatic injury or from improper or overuse of a muscle-tendon unit characterized by pain, swelling and impaired movement when using the injured muscles. Treatment includes cold or heat compresses, immobilization, and/or the use of NSAIDs.

Soft tissue injuries, such as sprains and strains, can affect any ligamentous or muscle-tendon structure and include, but are not limited to the ligaments and tendons associated with the following joints and structures: foot, plantar fascia, ankle, knee, patellar-femoral structure, hip, ilio-tibial band, back, shoulder, elbow, wrist, hand, jaw, and neck.

Hyaluronic acid (hereinafter, "HA"), also known as hyaluronan, hyaluronate or sodium hyaluronate, is an abundant non-sulfated glycosaminoglycan that is present in all joint tissues. HA is a naturally occurring linear polysaccharide composed of $\beta$-1,4-linked D-glucuronic acid-($\beta$-1,3)-N-acetyl-D-glucosamine dissacharide units. In its native form, HA exists as a high molecular weight polymer (about $10^6$-$10^7$ Da). In normal human synovial fluid, the molecular weight of HA is between about 6-7×$10^6$ Da, and the concentration is about 2-4 mg/ml. HA synthesized by synoviocytes is responsible for the viscoelastic properties of synovial fluid and plays a fundamental role in the maintenance of the trophic status of the cartilage. In joint disease there is a reduction in both the concentration and molecular weight of HA.

Intra-articular injection of exogenous high molecular weight HA (>5×$10^6$ Da) was found to improve function in humans with osteoarthritis or rheumatoid arthritis (Maheu et al., Int. J. Clin. Pract. 56:804-813, 2002; Matsuno et al., Inflamm. Res. 48:154-159, 1999). Three to five weekly intra-articular injections were required to significantly improve the pain and the functional status of patients with osteoarthritis, the effect lasting at least six months and up to one year after treatment cessation (Maheu et al., Int. J. Clin. Pract. 56:804-813, 2002). It was believed that intra-articular administration of HA may reverse HA degradation observed in osteoarthritis and to restore synovial fluid viscosity (viscosupplementation) (Balazs and Denlinger, J. Rheumatol. 20:3-9, 1993). Intra-articular administration of HA was also found to improve function in humans with acute knee injury (Zattono et al., Eur. J. Rheumatol. Inflamm. 15:53-69, 1995). While intra-articular administration of HA is has been proposed for various conditions, it is a complex process as locating the joint cavity during an intra-articular procedure is relatively difficult. Improper injection may lead to a variety of complications.

Peri-articular administration to treat joint injury has been described in European Patent No. 1677806 issued Nov. 19, 2008. The efficacy of periarticular administration of HA to patients with ankle sprain was shown to compare favourably with the efficacy obtained with celecoxib, an inhibitor of cyclooxygenase-2, or naproxen, an NSAID.

Another study (Petrella R J, Petrella M J, Cogliano A. Periarticular hyaluronic acid in acute ankle sprain. *Clinical Journal of Sports Medicine* 2007; 17(4):251-257) describes significant improvements in pain and function with HA injections in lateral ankle sprains in 158 athletes randomized to active treatment versus placebo. Not only was the effect greater than placebo, but this was associated with a high degree of satisfaction among patients in both in the short- and longer-term (3 months) as well as reduced pain and more rapid return to sport. However, the effect of peri-articular HA has a time of onset of about 4 days.

There is a lack of clear evidence to support use of Botulinum toxin in treatment of soft tissue injury. Botulinum toxin has been used in the treatment of many conditions, including detrusor instability, myofascial pain syndromes, dystonia, and writer's cramp. The direct impact of Botulinum toxin on pain pathways in many of these conditions suggest it may be helpful immediately on soft tissue pain. However, the results of it's reported use for treatment of lateral epicondylitis have not been encouraging. In one study (Hayton M J, Santini A J, Hughes P J, Frostick S P, Trail I A, Stanley J K. Botulinum toxin injection in the treatment of tennis elbow. A double-blind, randomized, controlled, pilot study. J Bone Joint Surg Am 2005; 87:503-507.), there was no observed difference between botulinum toxin injection and normal saline placebo in pain and grip strength. A side effect of botulinum toxin can be reduced function of soft tissue at the site of administration. A previous report (Wong S M, Hui A C F, Tong P Y, Poon D W F, Yu E, Wong L K S. Treatment of lateral epicondylitis with botulinum toxin. A randomized, double-blind, placebo-controlled trial. Ann Intern Med 2005; 143:793-797) describes unwanted side effects of minor paresis and weakness. Other sources of weakness may be secondary to neurotransmitter release dysfunction at the synaptic terminal. HA, on the contrary, injected locally at the site of injury has not appeared to have any precipitation of systemic risk of adverse events as well as any reported local adverse effects.

There are many reports of NSAID use for treating joint injury. NSAIDs effectively reduce pain and swelling and disability associated with joint injury, but this may not alter the clinical course of the ankle sprain regarding return to sport and may also cause significant adverse events, including gastrointestinal intolerance and serious events such as ulcers and bleeding.

Most known medical therapies for sprain and strain, whether directed to decreasing inflammation and/or pain, have proven to be less than adequate. There is a continuing need for novel compositions and methods for treating soft tissue and in particular, soft tissue injury such as sprain and strain.

SUMMARY OF THE INVENTION

According to an aspect of the invention there is provided a method for treating soft tissue in an animal, the method comprising administering a therapeutically effective amount of HA and a therapeutically effective amount of botulinum toxin at the site of said soft tissue.

According to another aspect of the invention there is provided a method for providing internal physical support to soft tissue in a mammal, the method comprising administering a therapeutically effective amount of HA and botulinum toxin around the site of said soft tissue. In aspects, the soft tissue is injured acutely or chronically. The injury may be from sprain and/or strain. In aspects the HA and botulinum toxin form an internal brace to internally support the injured soft tissue to allow it to heal and prevent further movement while healing is occurring.

According to another aspect of the invention there is provided a method for treating sub-dermal soft tissue in an animal, the method comprising administering a therapeutically effective amount of HA and a therapeutically effective amount of botulinum toxin at the site of said injured soft tissue.

According to another aspect of the invention there is provided a method for treating injured sub-dermal soft tissue in an animal, the method comprising administering a therapeutically effective amount of HA and a therapeutically effective amount of botulinum toxin at the site of said injured soft tissue.

According to another aspect of the invention there is provided a use of a therapeutically effective amount of HA and a therapeutically effective amount of botulinum toxin for preparation of a medicament for localized treatment of injured subdermal soft tissue in an animal.

According to yet another aspect of the invention there is provided a use of a therapeutically effective amount of HA and a therapeutically effective amount of botulinum toxin for localized treatment of injured subdermal soft tissue in an animal.

According to still another aspect of the invention there is provided a composition comprising a therapeutically effective amount of HA and a therapeutically effective amount of botulinum toxin for treatment of injured subdermal soft tissue.

According to still another aspect of the invention there is provided a composition comprising a therapeutically effective amount of HA and a botulinum toxin for treatment of soft tissue.

According to still yet another aspect of the invention there is provided a kit comprising a therapeutically effective amount of HA and a therapeutically effective amount of botulinum toxin for treatment of injured subdermal soft tissue. The kit may further comprise instructions for use and dosage regimes.

According to a further aspect of the invention there is provided a method for effectively treating ligamentous sprain or musculo-tendinous strain in an animal, including a human. In aspects, HA and botulinum toxin are administered by periarticular (peri-ligamentous, peri-fascial and/or peri-musculotendinous) administration. The HA and botulinum toxin may be provided as a composition.

According to another aspect of the invention is a composition to provide an internal brace or scaffold to soft tissue, wherein the composition comprises HA and botulinum toxin. In aspects, the composition is provided in a manner that surrounds the soft tissue to form a physical scaffold and support the tissue. In aspects, the soft tissue is injured acutely or chronically. In other aspects, the soft tissue may have undergone degradation such as in skin and the composition of the invention may be used to support and fill in the degradation.

Still a further aspect of the invention is to provide a method for treating sprain or strain that is minimally toxic to the recipient.

In another aspect of the invention there is provided a method for treating injured soft tissue by providing an internal physical support to said injured soft tissue in a mammal, the method comprising administering a therapeutically effective amount of HA and botulinum toxin around the site of said soft tissue, wherein said HA and botulinum toxin form a physical scaffold to support said injured soft tissue and immobilize said injured soft tissue such that further damage is minimal and said injured soft tissue may heal.

An even further aspect of the invention is to provide a method of synergistic HA and botulinum toxin treatment of sprain or strain in an animal, including a human.

Still another aspect of the invention is to provide a method that potentiates rehabilitation of a soft tissue injury, such as sprain or strain.

Another aspect of the invention is to provide a method that potentiates physical treatments of a soft tissue injury, such as sprain or strain.

Yet another aspect of the invention is to provide a method that potentiates the healing effect of heat or cold in the treatment of a soft tissue injury, such as sprain or strain.

Still another aspect of the invention is to provide a method that potentiates the healing effect of ultrasound in the treatment of a soft tissue injury, such as sprain or strain.

Another aspect of the invention is to provide a method that potentiates the healing effect of electrical stimulation in the treatment of a soft tissue injury, such as sprain or strain.

Yet another aspect is to provide a method that potentiates the healing effect of surgery in the treatment of a soft tissue injury, such as sprain or strain.

These and other objects, features and advantages of the present invention will become apparent after a review of the following detailed description of the disclosed embodiment and the appended claims.

BRIEF DESCRIPTION OF THE DRAWINGS

Embodiments will now be described, by way of example only, with reference to the attached Figures, wherein.

DETAILED DESCRIPTION

Figure 1:
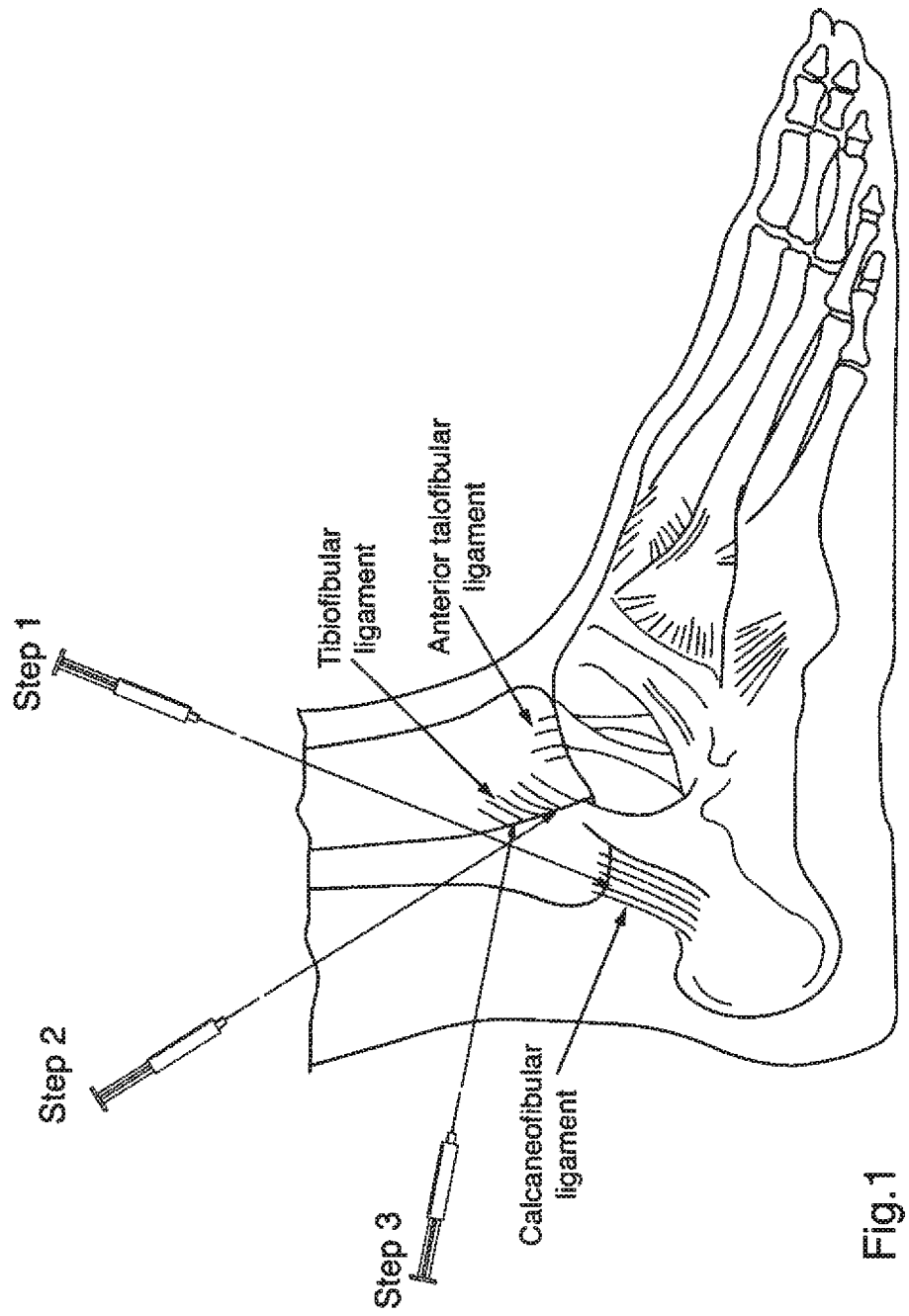
FIG. 1 is a diagram showing injection locations for the treatment of ankle sprain.

The invention describes the methods of treating soft tissue with the use of HA and botulinum toxin together to form a supportive physical scaffold around the desired soft tissue. The soft tissue is thus immobilized. In injured soft tissue accompanied by pain, the botulinum toxin may work directly on afferent pain receptors on the injured tissue as well as paralyzing the tissue so it won't undergo further damage post even. Thus the combination of HA and botulinum toxin is synonymous to an internal cast with additional pain relief.

In embodiments of the invention, methods are described for treating soft tissue injury, such as sprain and/or strain in a animal or human in need of such treatment. The method comprises the combined administration of hyaluronic acid and botulinum toxin. The hyaluronic acid and botulinum toxin is administered around the soft tissue to be treated. Soft tissue may be selected from, but not limited to, muscle, fascia, tendon and ligament. Soft tissue may also include fascia, fibrous tissues, fat and muscles. In aspects, the method comprises an administration mode selected from the group consisting of periarticular administration, peri-ligamentous administration, peri-fascial administration, peri-musculotendinous administration and combinations thereof.

The treatment of soft tissue injury such as sprains and strains can be done using HA and botulinum toxin around (i.e. "peri") injured soft tissue. Without wishing to be bound by theory, the peri-articular, peri-ligamentous, peri-fascial or peri-musculo-tendinous administration of HA to injured soft tissue or soft tissue susceptible to injury, such as injured or susceptible ligamentous or musculo-tendinous tissue, creates an internal scaffold or biocompatible internal support (i.e. an internal physical brace or scaffold) which provides structure and stability of form and function to the injured tissue thus allowing healing of the injured tissue to occur. This type of support provides protection to the site of injury by restricting further undesired or injurious movement at the site, and/or preventing further re-injury while healing is allowed to occur. Treatments directed to reducing inflammation and/or pain associated with soft tissue injury have been shown to have limited efficacy or significant side effects. HA can provide support to treat the trauma of an injured soft tissue, without directly affecting inflammatory or pain pathways. The botulinum toxin may act directly on afferent pain receptors on the injured tissue as well as paralyzing the tissue so it won't undergo further damage post acute event, such that is it like a true immobilization cast without the cast. The combination of the two (HA and botulinum toxin) together provides more support for than either alone for healing to occur.

Compositions described herein are relatively simple to prepare and administer. The HA remains stable over time and can be effective at dose regimens that are associated with minimal toxicity. Botulinum toxin can be prepared and administered consistent with prior reports, for example as described in U.S. Pat. No. 6,955,813 issued Oct. 18, 2005, US Patent Application Publication No 2004/0151741 published Aug. 5, 2004, or US Patent Application Publication No 2008/0292612 published Nov. 27, 2008 (the disclosures of which are incorporated herein by reference). Any one of the botulinum toxin types may be used, such as A, B, C1, C2, C3, D, E, F, G and combinations thereof. Botulinum toxin is also commercially available from Allergan Inc. under the tradename BOTOX™, from Ipsen Ltd. under the tradename DYSPORT™, and from Solstice Neurosciences under the tradename MYOBLOC™.

Compositions and methods described herein provide for treatment of an animal or human soft tissue and in particular, animal or human soft tissue injury, such as a sprain or strain using a combination of HA and Botulinum toxin.

In aspects, the HA and botulinum toxin may be provided as a composition comprising a suitable pharmaceutical carrier as is understood by one of skill in the art.

The method described herein is for treating injured soft tissue such as but not limited to muscle, fascia, tendons and ligaments. Soft tissue injury is treated by the administration of HA in a therapeutically effective amount and botulinum toxin in a therapeutically effective amount to alleviate the injury. The injury may be acute or chronic. The injury may involve any soft tissue, such as ligamentous or muscle-tendon structures including, but not limited to, the ligaments and tendons associated with the following joints and structures: foot, plantar fascia, ankle, knee, patellar-femoral structure, hip, ilio-tibial band, back, shoulder, elbow, wrist, hand, jaw, skin and neck. In certain examples, the injury may be an ankle sprain, lateral epicondylitis, or a shin splint where the anterior tibial muscle is torn away from the bone. The method described herein in aspects may be used for treatment of subdermal soft tissue, where treatment of skin, skin injuries or skin disorders is not intended. In other aspects, degradation of collagen in skin due to various reasons such as for example cortisol use or injury, may be treated with the compositions of the invention, dermal treatment.

The methods described herein may be used concomitantly with known treatments for sprain and/or strain commonly used by one of ordinary skill in the art. Such treatments include, but are not limited to, the use of non-steroidal anti-inflammatory drugs (NSAIDs), RICEs, plaster casts, braces, cyclooxygenase-2 inhibitors, corticosteroids, rehabilitation, physical therapies, heat and/or cold treatments, ultrasound, electrical treatments, surgery and combinations thereof.

The HA and botulinum toxin can be administered to the outside (i.e. around, "peri") of the injured soft tissue, in this manner it may be administered peri-articularly, peri-ligamentously and/or peri-musculotendinously. Methods of making periarticular injections are known to one of ordinary skill in the art. An example of a peri administration method is shown in FIG. 1. Such injections are generally subcutaneous and target the vicinity of a joint, especially near the insertions or origins of muscle tendons and ligaments (peri-ligamentous and/or peri-musculotendinous). While not wanting to be bound by the following statements, it is believed that the HA infiltrates around and between the tissues, at their interface, thereby supporting these tissues in a scaffold and acting as a form of an internal brace that helps during the healing process.

As used herein "hyaluronic acid (HA)" includes but is not limited to hyaluronan, hyaluronate, salts of HA, homologues, analogues, derivatives, complexes, esters, fragments, and subunits of HA that are effective to form an internal brace providing structure allowing healing to occur following administration to an injured soft tissue and to potentiate the activity of other therapeutic agents used for sprain and/or strain.

HA may be used in any variety of forms having different molecular weights as is understood by one of skill in the art. In aspects, the HA may have an average molecular weight of about 30-750 kDa, about 50-750 kDa, about 500-750 kDa, about 30 to more than 750 kDa, more than about 750 kDa, about 750-1200 kDa, more than about 500 kDa, or about 500-2000 kDa. These forms of HA may be free of species of HA below about 30 kDa. Other forms of HA that may be used include those forms having an average molecular weight of about 30-750 kDa, about 50-750 kDa, about 500-750 kDa, about 30 to more than 750 kDa, more than about 750 kDa, about 750-1200 kDa, more than about 500 kDa, or about 500-2000 kDa, and also include HA of molecular weight below about 30 kDa. In one embodiment, HA that may be used has an average molecular weight of about 30-750 kDa, about 50-750 kDa, about 500-750 kDa, about 30 to more than 750 kDa, more than about 750 kDa, about 750-1200 kDa, more than about 500 kDa, or about 500-2000 kDa., and also includes species of HA that are about 24 kDa.

In certain examples, the form of HA that may be used has an average molecular weight below 50 kDa, or below 30 kDa. In one embodiment, the HA that may be used has an average molecular weight of about 24 kDa. In another embodiment, HA may be used with an average molecular weight between about 0.3 kDa and 30 kDa. In another embodiment, HA may be used with an average molecular weight between about 10 kDa and 30 kDa.

HA is highly viscous, electronegative and hydrophilic. Various methods for the isolation, purification, fractionation or modification of HA are known to those skilled in the art. HA in its many forms is also readily available from many vendors or manufacturers as is understood by one of skill in the art such as Bioniche Life Sciences Inc, Canada; Anika Therapeutics, USA; Chemedica, Switzerland; Fidia, Italy; Genzyme (Biomatrix), USA; Hyalogic, USA; Hyalose, USA; Lifecore, USA; Seigakaku, Japan; Società Prodotti Antibiotici, Italy and Tedec Meiji, Japan. Specific hyaluronan compositions are also available for example from the following suppliers: BioMatrix Inc. Ridgefield, N.J. (Synvisc™, a 90:10 mixture of a hylan fluid and hylan gel); Fidia S.p.A., Abano Terme, Italy (Hyalgan™, the sodium salt of a rooster comb-derived hyaluronic acid (about. 500,000 to about 700,000 MW)); Kaken Pharmaceutical Co., Ltd., Tokyo, Japan (Artz™, a 1% solution of a rooster-comb derived hyaluronic acid, about 700,000 MW); Pharmacia AB, Stockholm, Sweden (Healon™, a rooster-comb derived hyaluronic acid, about $4 \times 10^6$ MW); Genzyme Corporation, Cambridge, Mass. (Surgicoat™, a recombinant hyaluronic acid); Pronova Biopolymer, Inc. Portsmouth, N.H. (Hyaluronic Acid FCH, a high molecular weight (e.g., about $1.5-2.2 \times 10^6$ MW) hyaluronic acid prepared from cultures of *Streptococcus zooepidemicus*; Sodium Hyaluronate MV, about $1.0-1.6 \times 10^6$ MW and Sodium Hyaluronate LV, about $1.5-2.2 \times 10^6$ MW); Calbiochem-Novabiochem AB, Lautelfingen, Switzerland (Hyaluronic Acid, sodium salt (1997 company catalog number 385908) prepared from *Streptococcus* sp.); Intergen Company, Purchase, N.Y. (a rooster-comb derived hyaluronic acid, $>1 \times 10^6$ MW); Diosynth Inc., Chicago, Ill.; Amerchol Corp., Edison, N.J.; Hyaltec Ltd., Scotland, UK) and Kyowa Hakko Kogyo Co., Ltd., Tokyo, Japan.

The therapeutic effectiveness of HA may be increased by methods including, but not limited to, chemically supplementing the HA, complexing the HA to biological or chemical carriers or coupling HA to tissue-type or cell-type directed ligands or antibodies.

As used herein, "botulinum toxin" includes a molecule possessing the biological activity of a protein toxin originally isolated from strains of Clostridium botulinum, including various immunotypes such as A, B, C1, C2, C3, D, E, F and G, and including analogs, derivatives, complexes, fusions, fragments and recombinant sources thereof as are known in the art.

As used herein, "biological activity of a protein toxin" includes muscle paralysis or an inhibition of exocytosis, in particular exocytosis of acetylcholine or another neurotransmitter.

Botulinum toxin can be prepared and administered consistent with prior reports, for example as described in U.S. Pat. No. 6,955,813 issued Oct. 18, 2005, US Patent Application Publication No 2004/0151741 published Aug. 5, 2004, or US Patent Application Publication No 2008/0292612 published Nov. 27, 2008 (the disclosures of which are incorporated herein by reference in their entirety). Botulinum toxin is also commercially available from Allergan Inc. under the tradename BOTOX™, from Ipsen Ltd. under the tradename DYSPORT™, and from Solstice Neurosciences under the tradename MYOBLOC™.

About 50 picograms of botulinum toxin (purified neurotoxin complex) serotype A is a LD50 in mice. One unit (U) of botulinum toxin is defined as the LD50 upon intraperitoneal injection into female Swiss Webster mice weighing 18-20 grams each. Several immunologically distinct botulinum toxins have been characterized, including botulinum toxin serotypes A, B, C1, C2, C3, D, E, F and G, each of which is distinguished by neutralization with serotype-specific antibodies. The different serotypes of botulinum toxin vary in the animal species that they affect and in the severity and duration of the paralysis they evoke. For example, it has been determined that botulinum toxin serotype A is 500 times more potent, as measured by the rate of paralysis produced in the rat, than is botulinum toxin serotype B. Additionally, botulinum toxin serotype B has been determined to be non-toxic in primates at a dose of 480 U/kg which is about 12 times the primate LD50 for botulinum toxin serotype A. Botulinum toxin is believed to bind with high affinity to cholinergic motor neurons, is translocated into the neuron and blocks the release of acetylcholine.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

The molecular weight for the known botulinum toxin serotypes, is about 150 kD. The naturally-occurring botulinum toxins are released by Clostridial bacterium as complexes comprising the 150 kD botulinum toxin along with associated non-toxin proteins. Thus, the botulinum toxin serotype A complex can be produced by Clostridial bacterium as 900 kD, 500 kD and 300 kD forms. Botulinum toxin serotype B and C1 are apparently produced as a 500 kD complex. Botulinum toxin serotype D has been shown to be produced as both 300 kD and 500 kD complexes. Finally, botulinum toxin serotype E and F have been shown to be produced as approximately 300 kD complexes. The complexes (i.e. molecular weight greater than about 150 kD) are believed to contain a non-toxin hemaglutinin protein and a non-toxin nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of subcutaneous injection of a botulinum toxin complex.

As used herein, "soft tissue injury" refers to damage of the soft tissue of the body. These types of injuries are a major source of pain and disability. The four fundamental tissues that are affected are the epithelial, muscular, nervous and connective tissues. Of these four tissues, compositions and methods described herein are primarily intended for treatment of muscular and connective tissues. Treatments described herein are in aspects intended for subdermal soft tissue injuries where skin is not included. Soft tissue injuries include, but are not limited to, sprains, strains, subluxation, repetitive stress injury, carpal tunnel syndrome, and the like.

As used herein, "structure" refers to structures associated with joints including, but not limited, to ligaments, fascia, tendons and muscles.

As used herein, "potentiates" relates to a degree of synergism that is greater than additive.

As used herein, "synergism" relates to the coordinated action of two or more agents.

As used herein, "an effective amount" is an amount sufficient to produce a therapeutic response. An effective amount may be determined with dose escalation studies in open-labeled clinical trials or bin studies with blinded trials. Administration of an effective amount of HA and botulinum toxin to an animal, including a human, is a therapeutic treatment that prevents, treats or eliminates an acute or chronic soft tissue condition including, but not limited to, sprain, strain and shin splints.

Methods described herein provide for administration of HA and botulinum toxin to treat injured soft tissue. The HA and botulinum toxin may be administered at separate times or concurrently. The HA and botulinum toxin may each be provided alone or as a composition comprising a pharmaceutically acceptable carrier. In certain examples, the HA and botulinum toxin can be administered around ("peri") an injured soft tissue, periarticularly, peri-ligamentously, peri-fascially and/or peri-musculotendinously to an animal, including humans.

Administration of HA and botulinum toxin compositions may be used alone or in conjunction with other therapeutic modalities used for the treatment of soft tissue injury to potentiate their effect. Such agents and methods include, but are not limited to, anti-inflammatory drugs, NSAIDs, corticosteroids, inhibitors of cyclooxygenase-2, RICE method, physical treatment, rehabilitation, heat and/or cold treatment, ultrasound therapy, electrical treatment such as piezoelectric and other forms of transcutaneous electrical treatment commonly used to treat musculoskeletal and joint injuries, elevation, compression, immobilization, immobilization devices, braces, plaster casts and surgery.

Preparation of Compositions

The method described herein comprises administration of HA and botulinum toxin. The HA and/or botulinum toxin may be administrated alone or may be formulated together or independently in a composition(s) comprising a pharmaceutically acceptable carrier including, but not limited to, a liquid carrier, a solid carrier or both.

Liquid carriers are aqueous carriers, non-aqueous carriers or both and include, but are not limited to, aqueous suspensions, dimethyl sulfoxide, ethanol, oil emulsions, water in oil emulsions, water-in-oil-in-water emulsions, site-specific emulsions, long-residence emulsions, sticky-emulsions, microemulsions and nanoemulsions. Solid carriers are biological carriers, chemical carriers or both and include, but are not limited to, particles, microparticles, nanoparticles, microspheres, nanospheres, bacterial cell wall extracts and biodegradable or non-biodegradable natural or synthetic polymers. Methods used to complex HA and/or botulinum toxin to a solid carrier include, but are not limited to, direct adsorption to the surface of the solid carrier, covalent coupling to the surface of the solid carrier, either directly or via a linking moiety, and covalent coupling or electrostatic coupling to the polymer used to make the solid carrier. HA and/or botulinum toxin can be stabilized, for example by the addition of non-ionic or ionic polymers such as polyoxyethylenesorbitan monooleates (TWEENs).

Aqueous carriers include, but are not limited to, water, saline and pharmaceutically acceptable buffers such as phosphate buffers. Non-aqueous carriers include, but are not limited to, a mineral oil or a neutral oil including, but not limited to, a diglyceride, a triglyceride, a phospholipid, a lipid, an oil and mixtures thereof, wherein the oil contains an appropriate mix of polyunsaturated and saturated fatty acids. Examples include, but are not limited to, soybean oil, canola oil, palm oil, olive oil and myglyol, wherein the fatty acids can be saturated or unsaturated. Optionally, excipients may be included regardless of the pharmaceutically acceptable carrier used. These excipients include, but are not limited to, anti-oxidants, buffers, and bacteriostats, and may include suspending agents and thickening agents.

Kits

HA and botulinum toxin can be provided together in a kit. The kit comprises a therapeutically effective amount of HA and a therapeutically effective amount of botulinum toxin. The HA and the botulinum toxin can be provided in separate containers as separate compositions or within the same container as part of a single composition. Each HA and/or botulinum toxin composition provided in the kit can include a pharmaceutically acceptable carrier. The kit can further comprise instructions for use of the kit. For example, the kit can comprise instructions for localized administration of the HA and the botulinum toxin for treatment of acutely or chronically injured soft tissue in an animal. The instructions may be specifically directed to injured soft tissue selected from the group consisting of muscle, fascia, tendon and ligament. In another example, the kit may comprise instructions for peri-articular, peri-ligamentous, peri-musculotendinous or peri-fascial administration of the HA and the botulinum toxin.

Combination Therapy

HA and botulinum toxin may each be administered alone, in a composition and further in combination with other therapeutic modalities including, but not limited to, anti-inflammatory drugs, NSAIDs, corticosteroids, inhibitors of cyclooxygenase-2, RICE method, physical treatment, rehabilitation, heat and/or cold treatment, ultrasound therapy, electrical treatment, elevation, compression, immobilization, immobilization device, braces, plaster casts and surgery. These therapeutic agents such as anti-inflammatory drugs, NSAIDs, corticosteroids, and inhibitors of cyclooxygenase-2 are administered using dosages and routes known to one of ordinary skill in the art. For example, anti-inflammatory drugs, NSAIDs, corticosteroids, and inhibitors of cyclooxygenase-2 may be administered orally. Corticosteroids may also be administered intravenously, topically, into a joint or through other routes known to one of ordinary skill in the art of administering corticosteroids.

The route of administration of HA and botulinum toxin includes, but is not limited to, periarticular, peri-ligamentous, peri-fascial or peri-musculotendinous injection. Any suitable device such as a syringe may be used to administer the HA and botulinum toxin, or HA and botulinum toxin composition(s) as is known to one of skill in the art.

HA and botulinum toxin may be dosed according to known methods. The amount of HA administered per dose is from about 0.001 to 1000 mg, more specifically from about 0.1 to 100 mg, from about 1 to 10 mg, and from about 0.1 mg to 5 mg. The volume per dose may be about 0.01 to 5.0 ml per dose, and in aspects from about 0.1 to 2.0 ml per dose, about 0.5 to 1.0 ml per dose or 0.01 to 1.0 ml per dose. The concentration of the HA provided in the composition may be in the range of about 5 to 100 mg/ml of the solution, in aspects 5 to 50 mg/ml of the solution and any range therebetween. The administration usually occurs in the vicinity of a soft tissue injury, such as a sprain, strain or shin splint.

One skilled in the art can determine the appropriate dose and frequency of administration(s) to achieve an optimum clinical result. That is, one of ordinary skill in medicine would be able to administer the appropriate amount of the botulinum toxin at the appropriate time(s) to effectively treat the injured soft tissue(s). The dose of the toxin to be administered depends upon a variety of factors, including the size of the soft tissue, the severity of the soft tissue injury, the type and/or source of the botulinum toxin, and the like. For example, from about 0.1 U/kg to about 15 U/kg, of botulinum toxin type A can be administered to the injured soft tissue. As another example, about 1 U/kg to about 20 U/kg of botulinum toxin type A may be administered to the injured soft tissue. In other examples, use of from about 0.1 U/kg to about 30 U/kg of a botulinum toxin type A and from about 1 U/kg to about 150 U/kg of a botulinum toxin type B is contemplated for methods described herein. With regard to the other botulinum toxin serotypes (including toxin types E and F) examples of the U/kg dosage to be used fall within the range of about 0.1 U/kg to about 150 U/kg.

Since its introduction as a therapeutic agent, the pharmaceutical measurement of the denervating or biologic activity of botulinum toxin has been the LD50 unit using a 18-22 gram Swiss-Webster mouse, quantitated statistically by injecting cohorts of mice at different dilutions from the purified botulinum toxin protein or its protein complexes. This measurement has the advantage of simplicity of a clear endpoint determination (living or dead mouse). The LD50 unit dose is known to vary depending on the botulinum toxin immunotype when compared in clinical studies. For example, one preparation of type B botulinum toxin (MYOBLOC™) requires 5,000-15,000 LD50 units to treat torticollis whereas another preparation of botulinum toxin Type A (BOTOX™) requires only 100-300 LD50 units. Similarly, the LD50 unit can vary between different sources of the same botulinum toxin immunotype. For instance, approximately 50-300 units of BOTOX™ is required to treat blepharospasm and cervical dystonia compared to 200-1200 units of DYSPORT™, another preparation of botulinum type A toxin. One of skill in the art can take such variables into account when preparing a dosing regimen.

The administration of HA and botulinum toxin or HA and botulinum toxin plus other therapeutic modalities, the amount per dose, the dose schedule and the method of administration should be decided by the practitioner using methods known to those skilled in the art and will depend on the type of injury, the severity of the injury, the location of the injury and other clinical factors such as the size, weight and physical condition of the recipient. As such, the HA and botulinum toxin may be administered together or independently once, twice or several times as directed by the physician in amounts and concentrations as directed by the physician. The HA and botulinum toxin or HA and botulinum toxin plus other therapeutic agents or methods can be administered or applied in a single dose treatment, in multiple dose treatments or continuously infused on a schedule and over a period of time appropriate to the injury being treated, the condition of the recipient and the route of administration. Moreover, the botulinum toxin and HA may be administered together or the botulinum toxin can be administered or applied before, at about the same time as, or after administration of HA. Similarly, the therapeutic agents or methods can be administered or applied before, at the same time as, or after administration of each of HA and botulinum toxin.

The following examples will serve to further illustrate the present invention without, at the same time, however, constituting any limitation thereof.

EXAMPLE 1

HA and Botulinum Toxin Preparation

Hyaluronic acid was supplied in a single dose vial containing 1% Hyaluronic acid sodium salt solution with an average molecular weight of 500-2000 kilodaltons (Hyaltec, Scotland, UK) in enough excipient to make a total volume of 1.5 cc. Vials were stored at room temperature (10-30° Celsius). Botulinum toxin was provided as 60 units (in 1 cc) of Botox (Allergan, US). Total volume of hyaluronic acid and Botox was 2.5 cc.

EXAMPLE 2

Efficacy of HA and Botulinum Toxin on Ankle Sprain Following Periarticular Administration Ankle sprains are among the most common of all sports injury with approximately 2 million people per year seeking medical treatment. Data from the National Hospital Ambulatory Medical Care survey 2000 emergency department summary list of 1.375 million emergency department visits in the United States alone attributable to ankle sprains representing about 1.3% of all visits. Hence, the economic impact of these injuries is high. Ankle sprains are most commonly affecting the lateral ligament complex (anterior talofibular, posterior talofibular, and calcaneofibular). These are secondary to varus or inversion sprains, including a spectrum of symptoms and severity such as pain, swelling, tenderness, loss of function typically defined as 1st, 2nd or 3rd degree. Most ankle sprains are of the 1st or 2nd degree or mild-to-moderate in symptom intensity.

Treatment guidelines are not consistent, however, the American Academy of Orthopedic Surgeons recommends that an initial rehabilitation program of up to three weeks begin with non-steroidal anti-inflammatory medications, rest, ice, compression and elevation (RICE), protected weight bearing, early mobilization and isometric exercise. This treatment regimen, being conservation, may limit disability to an average of 8-10 days for 1st degree and 2-3 weeks for a 2nd degree sprain. However, this approach may not modify the degree of the disability or the recovery period. In one study of ankle sprain, pain and dysfunction were found to persist up to 16-18 months after the initial sprain in 73% of patients with additionally 40% reporting an inability to walk and 11% continuing to use medications for ankle pain symptoms. In a long-term follow up study, 40% of patients reported residual long-term symptoms and dysfunction even 6.5 years after the initial ankle sprain.

NSAIDs effectively reduce pain and swelling and disability associated with ankle sprain, but this may not alter the clinical course of the ankle sprain regarding return to sport and may also cause significant adverse events, including gastrointestinal intolerance and serious events such as ulcers and bleeding.

Methods:

A double-blind, placebo-controlled trial of HA combined with botulinum toxin compared to HA alone, botulinum toxin alone, and placebo was conducted.

Ethics Review Board approval was obtained and all patients gave written and informed consent. The study was conducted from March 2004 until December 2007 where consecutive patients were recruited from three primary care sport medicine facilities in Ontario, Canada. The total number of ankle sprains at these facilities during the two years prior to this study was 1,174. Study physicians and personnel attended a prestudy investigatory meeting to ensure standardization of study procedures, data collection and management. The study was conducted according to the Declaration of Helsinki Good Clinical Practice Guidelines.

Patients were screened in the clinic, according to selected inclusion/exclusion criteria. Eligibility inclusion criteria included: 18 years of age and older, 1st and 2nd degree lateral ankle sprain within 48 hours before enrolment in the study, a reported moderate or >4.5 cm. ankle pain on full weight bearing on a patient assessment of ankle pain using a 10 cm. Visual Analogue Scale (VAS), and availability for the duration of the study (12 months). Exclusion criteria included: bilateral ankle sprain, ipsilateral knee injury, 3rd degree ankle sprain, previous ankle sprain within six months, patients who had recently used anti-inflammatory medications, muscle relaxants, psychotropic medications that could confound the results, patients with a history of severe gastrointestinal, renal or hepatic disease, patients with rheumatic diseases (including osteoarthritis), history of drug or alcohol abuse, pregnant or lactating women of childbearing potential not willing to use an acceptable form of contraceptive during the study, or having received an investigational product within 30 days of first study visit.

Screening Ankle Sprain:

Diagnosis of 1st or 2nd degree ankle sprain was made by athletic trainers affiliated with the university athletic programs, emergency physicians at affiliated local hospitals, and family physicians in the referral base who then sent patients within 48 hours to the sport medicine clinics. Patients were asked to participate in the study and required to report within 48 hours of their injury. This visit was followed provision of informed consent and then a screening assessment and physical examination by a study physician. Pain at enrolment, as assessed by the Visual Analogue Scale, for eligibility required >4.5 cm. on a 0-10 cm. scale. Patients were then randomized 1:4 to one of the four treatment groups using a computer generated randomization schedule: 1) periarticular HA molecular weight range 500-2000 kilodaltons (20 mg.) plus botulinum toxin (60 units Botox), 2) peri-articular HA molecular weight range 500-2000 kilodaltons (20 mg.) alone, 3) botulinum toxin (60 units Botox) alone, and 4) normal saline. All patients were also advised regarding standard support measures including RICE (rest, ice, compression, elevation).

Assessments were done at baseline and on Days 4, 8, 30, 90, and 12 months as summarized in Table 1. Efficacy measures for ankle sprain included patient's VAS of pain on weight bearing (0-10 cm) and walking 20 meters (0-10 cm), patient's global assessment of ankle injury (5. categorical scale), patient's assessment of return to normal function/activity and sport (5. categorical scale), patient's satisfaction assessment (10. categorical scale), number of days to full return to sport activity (days), adverse events as defined by the World Health Organization. At the baseline (within 48 hours of ankle sprain), patients had full examination as well as an x-ray to exclude other pathology.

TABLE 1

Ankle Sprain Schedule of Time and Events

| Evaluations | Baseline/ Day 1 | Day 4 | Day 8 | Day 30 | Day 90 | Day 356 |
|---|---|---|---|---|---|---|
| Informed Consent | X | | | | | |
| Medical History | X | | | | | |
| Vital Signs and Physical Exam | X | | | | | X |
| X-Ray Evaluation | X | | | | | |
| Patients VAS of pain on weight bearing | X | | X | X | X | X |
| Patients VAS of pain on walking (20 m) | X | | X | X | X | X |
| Patients global assessment of ankle injury | X | | X | X | X | X |
| Patients assessment of normal function/activity | X | | X | X | X | X |
| Patients satisfaction assessment | | | X | X | X | X |
| Number of days to return to sport | | | X | X | X | X |
| Treatment Administration | X | | | | | |
| Concomitant Medications | X | X | X | X | X | X |
| Adverse Events | | X | X | X | X | X |

Treatment Phase:

After outcome assessment, those randomized to treatment received single injection of: HA+Botox (1.5 cc HA+60 units Botox 1.0 cc), HA alone (1.5 cc), Botox (60 units, 1.0 cc) alone, or placebo (normal saline 2.5 cc).

Peri-articular injections for treatment of ankle sprain were performed using previously described technique (Petrella R J, Petrella M J, Cogliano A. Periarticular hyaluronic acid in acute ankle sprain. *Clinical Journal of Sports Medicine* 2007; 17(4):251-257). Briefly, an injection was delivered using a single penetration along three planes in the anterior-posterior, medial, and lateral to proximal ligamentous landmark (FIG. 1). All assessments and injections were repeated on Day 4 (±one day). Rescue medication (500 mg. acetaminophen tablets of up to 4 tablets per day) was allowed in all groups but were held for the 24 hours prior to each study visit. Syringes were concealed using taping as well as modified syringe to approximate similar pressures exerted on act of injection. This has been previously described (Petrella R J, Petrella M J, Cogliano A. Periarticular hyaluronic acid in acute ankle sprain. *Clinical Journal of Sports Medicine* 2007; 17(4):251-257). Patients were free to withdraw from the trial anytime.

Follow up assessments were completed on Days 8, 30, 90 and 12 months. Day 8 (±two days), Day 30 (±seven days), Day 90 (±seven days), and 12 months (±seven days). Adverse events and concomitant medications were assessed throughout the patient's participation in the study.

Outcome Measures:

The primary efficacy outcome was VAS of pain on weight bearing in ankle sprain at Day 8. Secondary efficacy outcomes included: VAS with pain on walking 20 meters, patient's global assessment of ankle injury, patient's assessment of return to normal function/activity in sport, patient's satisfaction assessment, and number of days to return to full sport.

Patients were also prescribed rescue medication (500 mg. Acetaminophen tablets up to four tablets per day), but to be held 24 hours prior to each study visit.

Study Materials:

Hyaluronic acid was supplied in a single dose vial containing 1% Hyaluronic acid sodium salt solution with an average molecular weight of 500-2000 kilodaltons in enough excipient to make a total volume of 1.5 cc. Vials were stored at room temperature (10-30° Celsius). Normal saline was provided at 2.5 cc. Botulinum toxin was provided as 60 units Botox (Allergan, US) in 1 cc.

Safety Assessment:

During treatment—follow up phases to evaluate safety, assessment of adverse events (throughout the study) and vital signs were conducted on all patients who received at least one dose of the study products.

Statistical Analysis:

Sample size for ankle sprain was determined to allow detection of 20 mm difference in weight bearing VAS on Day 8 assuming a standard deviation of less or equal to 10 mm of the mean distribution, $\alpha$ of 5%, and a $\beta$ level of 10%, giving a statistical power of 90%. With a potential dropout rate of about 10%, we estimated a sample size of 150 patients.

Demographic and baseline data were compared within the four groups using students' t-test for continuous variables and chi square statistics for non-continuous variables. Statistical analysis was based on intent-to-treat (ITT) population. Efficacy and safety variables were analyzed between groups using appropriate statistical methods, including students' t-test for quantitative variables, chi square test for nominal variables, Mann-Whitney U test for ordinal variables. The data analysis was performed using a SAS version 8.0 (SAS Institute, Carey, N.C.). All statistical tests were two-tailed with a 5% level of significance.

The primary efficacy endpoint for the ankle sprain were decrease in pain on weight bearing by Day 8. Adverse events were listed individually and summarized by body system.

Results:

A total of 500 patients were screened and the intent-to-treat population was 258 patients. Reasons for non-participation in the study included not being available for the study period, concomitant injury, use of NSAIDs, previous ankle sprain within six months, and aversion to injections. Average age of the study population for ankle sprain was 26 ($\pm$7 years). There were equal male/female representations between groups in the ankle sprain study. There were no differences between the groups at baseline for concomitant conditions nor were there any differences in administration of injections between groups. 100% compliance for the injection series was obtained throughout treatment phases. The time to intervention in the ankle sprain study was 38 ($\pm$4 hours). Seven patients in the ankle sprain study failed to follow up at 90 days and 21 patients at 12 months. Reasons for failure to follow up were non-efficacy of treatment, move outside of study site, and failure to return for unknown reasons. All those who failed to return were students in the university population (transient).

Global Therapeutic Response:

Patient satisfaction with treatment scores among subjects showed 92% versus 48% favouring HA+Botox vs placebo, 77% versus 57% for HA vs placebo, 74% versus 57% for Botox vs placebo. There was a statistical difference between HA+Botox vs all other groups. This was consistent for Days 4, 8, 30, 90 and 12 month follow up (chi square test, $p<0.0001$) (Table 2).

Tolerance:

Six adverse events were observed among all subjects including two in the HA+Botox, two in the Botox, one in the placebo, and one in the HA groups. Adverse events included mild erythema, mild paresthesia around the ankle at Day 4 with no residual effects beyond Day 8. Pain for adverse events in all four groups did not differ in intensity. No adverse events were reported for the remaining study visits at Day 8, 30, 90 and 12 months. There were no serious adverse events.

Efficacy:

Primary criterion for the decrease from baseline to Visit 2 (Day 8—$\pm$1) in weight bearing pain calculated in the intent-to-treat population are shown in Table 2. The changes from baseline to Visit 1 (Day 4) in weight bearing pain were:
- −7.1 ($\pm$1.1) for HA+Botox;
- −2.4 ($\pm$1.18) for HA alone;
- −2.4 ($\pm$1.2) for Botox alone; and
- −1.3 ($\pm$1) for placebo.

For walking pain at Visit 1 (Day 4):
- −6.6 ($\pm$1.4) for HA+Botox;
- −4.3 ($\pm$2.0) for HA alone;
- −3.5 ($\pm$1.8) for Botox alone; and
- −1.76 ($\pm$2.4) for placebo.

For Visit 2 (Day 8), Visit 3 (Day 30), Visit 4 (Day 90), and Visit 5 (Day 356), statistical significance was achieved ($p<0.001$) for HA+Botox versus placebo as well as versus all of the other treatments for both VAS weight bearing and VAS walking.

TABLE 2

Ankle sprain subject characteristics, efficacy and safety outcomes.

| Characteristics | Double-blind treatment phase | | | | | |
|---|---|---|---|---|---|---|
| | Baseline (n = 258) | Day 4 (n = 256) | Day 8 (n = 256) | Day 30 (n = 255) | Day 90 (n = 252) | Day 356 (n = 250) |
| VAS Pain of Weight Bearing (change in cm from baseline), Mean (SD) | | | | | | |
| HA + Botox | 8.3 (1.1) | −7.1 (1.1)*+ | −7.2 (1.5)*+ | −7.7 (1.0)*+ | −8.2 (1.1)*+ | −8.3 (1.2)*+ |
| Botox | 8.1 (1.4) | −2.4 (1.2) | −2.5 (1.1) | −2.8 (1.1) | −3.0 (2.1) | −6.4 (2.0) |
| HA | 7.9 (1.1) | −2.46 (1.18)*+ | −3.0 (1.7) | −3.41 (1.62)*+ | −3.7 (1.22)*+ | −6.01 (2.31)*+ |
| PL | 8.0 (1.5) | −1.13 (0.17) | −1.5 (2.0) | −2.38 (1.72)* | −2.42 (1.09)* | −6.1 (1.222)* |
| VAS Pain on Walking (change in cm from baseline), Mean (SD) | | | | | | |
| HA + Botox | 8.9 (1.1) | −6.6 (1.4)*+ | −8.6 (1.0)*+ | −8.9 (0.1)*+ | −8.8 (0.1)*+ | −8.8 (0.1)*+ |
| Botox | 9.1 (0.9) | −3.5 (1.8) | −3.2 (1.8) | −3.4 (0.4) | −3.6 (1.1) | −2.9 (1.1) |

TABLE 2-continued

Ankle sprain subject characteristics, efficacy and safety outcomes.

| Characteristics | Double-blind treatment phase | | | | | |
| --- | --- | --- | --- | --- | --- | --- |
| | Baseline (n = 258) | Day 4 (n = 256) | Day 8 (n = 256) | Day 30 (n = 255) | Day 90 (n = 252) | Day 356 (n = 250) |
| HA | 8.8 (1.0) | −4.33 (2.02) | −3.9 (1.9) | −5.62 (2.54) | −5.68 (2.55)* | −5.10 (1.92)* |
| PL | 9.0 (0.5) | −1.76 (2.43) | −1.1 (2.3) | −1.2 (1.16)* | −2.67 (1.89)* | −3.78 (1.99)* |

All secondary efficacy parameters improved during the study in all groups. However, intergroup comparisons showed a statistically significant difference in favour of HA+Botox compared to other treatments after Visit 1 on all efficacy parameters. Hence, the secondary efficacy variables were globally consistent with those concerning the primary outcome.

In the current study, the findings for HA+Botox are unexpected. The HA+Botox group had significantly improved primary and secondary outcomes at 4 days, 8 days, 30 days, 90 days and 12 months compared to all other groups. The magnitude of improvement exceeded the sum of either treatment alone. Further, patient satisfaction was also significantly greater in the HA+Botox group at 4 days and 8 days. Findings in the HA group were similar to those previously reported (Petrella R J, Petrella M J, Cogliano A. Periarticular hyaluronic acid in acute ankle sprain. *Clinical Journal of Sports Medicine* 2007; 17(4):251-257). showing consistency of methodology. Hence, an alternative, novel therapy for acute ankle sprain has been developed and validated. This treatment resulted in improved return to sport and had few and similar minor adverse effects to placebo while the primary and secondary outcomes improved more than any treatment described in the literature to date.

The results showed not only positive, but unexpectedly superior improvement with HA and Botox compared to either treatment alone. Further, this novel therapy showed very few adverse effects that were similar to placebo. Faster return to sport with HA+Botox is certainly of importance to those faced with returning to competitive levels of sport earlier in their rehabilitation. The results up to 12 months suggest that the superior improvement with HA+Botox continue to exceed those of other treatments and may result in fewer injuries in the longer term. Long-term follow up suggests that the chronic safety of this treatment is observed and further investigation including combinations of HA and Botox in other soft tissue trauma models are underway. Further investigation should also include those patients presenting with more chronic nature of their disability, including chronic, recurrent ankle sprain.

EXAMPLE 3

Efficacy of HA and Botulinum Toxin on Lateral Epicondylitis Following Periarticular Administration Tennis elbow (lateral epicondylitis) is a common cause of elbow pain and wrist extensor dysfunction in adults, affecting about 1-3% of the general population yearly. Localized tenderness around the lateral epicondyle generally characterizes the condition while pain is reproduced by resistant extension of the wrist or middle finger with the elbow in a straight extended position. Tennis elbow or lateral epicondylitis is common in upper extremity sport activities, including golf and tennis. It results in significant morbidity and time away from sport. There is currently no consensus on optimal treatment, however, topical or oral NSAIDs are often recommended for short-term pain relief. Corticosteroid injections have been shown to be beneficial at least temporarily, but carry the risk of adverse events. These are also matched by adverse events as a result of both topical and oral NSAIDs use.

Methods:

A double-blind, placebo-controlled trial of HA combined with botulinum toxin compared to HA alone, botulinum toxin alone, and placebo was conducted.

Ethics Review Board approval was obtained and all patients gave written and informed consent. The study was conducted in March 2004 until December 2007 where consecutive patients were recruited from three primary care sport medicine facilities in Ontario, Canada. The total number of lateral epicondylitis presentations at these facilities during the two years prior to this study was 310. Study physicians and personnel attended a prestudy investigatory meeting to ensure standardization of study procedures, data collection and management. The study was conducted according to the Declaration of Helsinki Good Clinical Practice Guidelines.

The lateral epicondylitis study inclusion criteria included: pain on the lateral side of the elbow that had persisted >4.5 cm. on a 10 cm. VAS with the wrist and elbow in full extension greater than two weeks but less than three months. Exclusion criteria included: previous local injections including corticosteroids or acupuncture or HA, nerve entrapment, pregnancy, breast feeding, systemic neuromuscular disorders, or current use of anti-inflammatory medications, muscle relaxants or psychotropic medications, patients with severe history of gastrointestinal, renal or hepatic disease, patients with rheumatic diseases (including osteoarthritis), history of drug or alcohol abuse. Patients were also excluded if they had participated in a previous investigational product within 30 days of the first study visit.

Screening Lateral Epicondylitis:

In the lateral epicondylitis group, patients were referred by family physicians and self-referral to the sport medicine clinics. Screening included assessment by a study physician confirming lateral elbow pain longer than two weeks and less than three months, particularly exacerbated during resisted dorsiflexion of the wrist with the elbow in full extension with a VAS score >4.5 cm on a 0-10 cm VAS. Patients were then randomized 1:4 to one of the four treatment groups using a computer generated randomization schedule: 1) periarticular HA molecular weight range 500-2000 kilodaltons (20 mg.) plus botulinum toxin (60 units Botox), 2) peri-articular HA molecular weight range 500-2000 kilodaltons (20 mg.) alone, 3) botulinum toxin (60 units Botox) alone, and 4) normal saline. All patients were also advised regarding standard support measures including RICE (rest, ice, compression, elevation).

Assessments were done at baseline and on Days 8, 30, 90, and 12 months as summarized in Table 3. Efficacy measures for lateral epicondylitis included patient's VAS of pain on grip (0-10 cm), grip strength, patient's global assessment of injury (5. categorical scale), patient's assessment of return to normal function/activity and sport (5. categorical scale), patient's satisfaction assessment (10. categorical scale), adverse events as defined by the World Health Organization.

TABLE 3

Lateral Epicondylitis Schedule of Time and Events

| Evaluations | Baseline/ Day 1 | Day 8 | Day 30 | Day 90 | Day 356 |
|---|---|---|---|---|---|
| Informed Consent | X | | | | |
| Medical History | X | | | | |
| Vital Signs and Physical Exam | X | | | | X |
| X-Ray Evaluation | X | | | | |
| Patients VAS of pain on grip | X | X | X | X | X |
| Grip strength (N) | X | X | X | X | X |
| Patients global assessment of injury | X | | X | X | X |
| Patients assessment of normal function/activity | X | | X | X | X |
| Patients satisfaction assessment | | | X | X | X |
| Treatment Administration | X | | | | |
| Concomitant Medications | X | X | X | X | X |
| Adverse Events | | X | X | X | X |

Treatment Phase:

After outcome assessment, those randomized to treatment received single injection of: HA+botox (1.5 cc HA+60 units Botox, 1.0 cc), HA alone (2.0 cc), Botox alone (60 units, 1.0 cc), or placebo (normal saline 2.5 cc).

Figure 2:
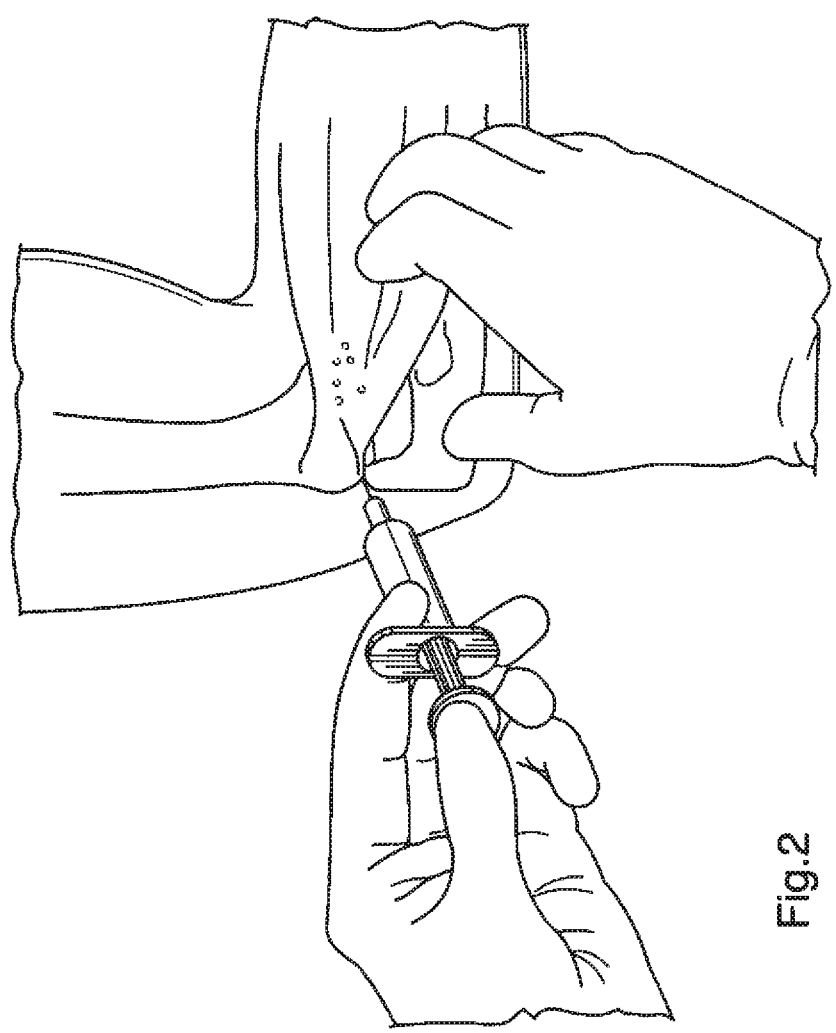
FIG. 2 is a diagram showing injection locations for the treatment of lateral epicondylitis.

For the lateral epicondylitis injections, patients flexed the affected arm resting on a firm surface with the investigator administering the injection deeply into the subcutaneous tissue and muscle 1 cm. from the lateral epicondyle toward the primary point of pain (FIG. 2). Syringes were concealed using taping as well as modified syringe to approximate similar pressures exerted on act of injection. This has been previously described (Petrella R J, Petrella M J, Cogliano A. Peri-articular hyaluronic acid in acute ankle sprain. *Clinical Journal of Sports Medicine* 2007; 17(4):251-257).

Follow up assessments were completed on Days 8, 30, 90 and 12 months. Day 8 (±two days), Day 30 (±seven days), Day 90 (±seven days), and 12 months (±seven days). Adverse events and concomitant medications were assessed throughout the patient's participation in the study.

Outcome Measures:

In lateral epicondylitis, the primary endpoint was pain intensity using 10 cm VAS ranging from 0-10 cm at rest. Secondary outcomes included: grip strength using a jamar hydraulic hand dynamometer (Sammons Preston, Bolingbrook, Ill.), patient global assessment of tennis elbow injury, patient satisfaction, number of days to return to full sport. Assessment was conducted with the patient's elbow fully extended and the dynamometer's handle in the middle position. Patients performed three grip tests on the affected arm with a mean score calculated and use for analysis. Grip strength and VAS scores were recorded at baseline, 8 days, 30 days, 90 days, and 12 months. Patients were also prescribed rescue medication (500 mg. Acetaminophen tablets up to four tablets per day), but to be held 24 hours prior to each study visit.

Study Materials:

Hyaluronic acid was supplied in a single dose vial containing 1% Hyaluronic acid sodium salt solution with an average molecular weight of 500-2000 kilodaltons in enough excipient to make a total volume of 1.5 cc. Vials were stored at room temperature (10-30° Celsius). Normal saline was provided at 2.5 cc. Botox was provided as 60 units (Allergan, US) in 1 cc.

Safety Assessment:

During treatment—follow up phases to evaluate safety, assessment of adverse events (throughout the study) and vital signs were conducted on all patients who received at least one dose of the study products.

Statistical Analysis:

For the lateral epicondylitis study, a sample size of 60 was estimated to be needed to achieve an 80% statistical power to detect a 40% difference in the VAS scores between the combined HA and Botox treatment and either treatment alone treatment groups at a statistical significance level of 0.05, a of 5% at 8 days. Estimates were based on findings from a previous study (Wong S M, Hui A C F, Tong P Y, Poon D W F, Yu E, Wong L K S. Treatment of lateral epicondylitis with botulinum toxin. A randomized, double-blind, placebo-controlled trial. Ann Intern Med 2005; 143:793-797) comparing corticosteroid with placebo, which reported a 40% difference in VAS scores. The statistical power is also based on the previous study by Wong et al. (Wong S M, Hui A C F, Tong P Y, Poon D W F, Yu E, Wong L K S. Treatment of lateral epicondylitis with botulinum toxin. A randomized, double-blind, placebo-controlled trial. Ann Intern Med 2005; 143: 793-797).

Demographic and baseline data was compared within the four groups using students' t-test for continuous variables and chi square statistics for non-continuous variables. Statistical analysis was based on intent-to-treat (ITT) population. Efficacy and safety variables were analyzed between groups using appropriate statistical methods, including students' t-test for quantitative variables, chi square test for nominal variables, Mann-Whitney U test for ordinal variables. The data analysis was performed using a SAS version 8.0 (SAS Institute, Carey, N.C.). All statistical tests were two-tailed with a 5% level of significance.

Results:

A total of 100 patients were screened and the intent-to-treat population was 88 patients. Reasons for non-participation in the study included not being available for the study period, concomitant injury, use of NSAIDs, and aversion to injections. Average age of the study population for the lateral epicondylitis study was 49 years (±12 years). There were more women than men in the lateral epicondylitis study but the difference was not significant, as determined statistically using baseline characteristics. There were no differences between the groups at baseline for concomitant conditions nor were there any differences in administration of injections between groups. 100% compliance with the injection series was obtained throughout the treatment phases. The time to intervention in the lateral epicondylitis study was 32 days (±18 days). Six patients in the lateral epicondylitis study failed to follow up at 90 days and 18 patients at 12 months. Reasons for failure to follow up were non-efficacy of treatment, move outside of study site, and failure to return for unknown reasons. All those who failed to return were students in the university population (transient).

Global Therapeutic Response:

Patient satisfaction with treatment scores among subjects showed that 88% vs. 21% favouring HA+Botox vs placebo, 53% vs 20% for HA vs placebo, 49% vs 18% for Botox vs placebo. There was a statistical difference between HA+Botox vs all other groups. This was consistent for Days 8, 30, 90 and 12 month follow up (chi square test, p<0.0001) (Table 4).

Tolerance:

In the lateral epicondylitis study, four patients in the HA+Botox group had mild paresthesia at the site of injection at 8 days, while three patients had similar symptoms at 8 days in the Botox. There were no Adverse Events reported in the other groups. There was no persistent weakness or paresthesia beyond Day 8.

Efficacy:

The primary efficacy outcome was VAS pain on hand grip at Visit 2 (Day 8), Table 4. The change on handgrip from baseline at Visit 2 was:
- −6.7 (±2.0) for HA+Botox;
- −3.1 (±1.5) for HA alone;
- −2.7 (±2.0) for Botox alone;
- −1.0 (±1.9) for placebo.

The VAS improved at Visit 3 to Visit 5 only in the HA+Botox group. Total grip also increased in the HA+Botox at each visit as did patient satisfaction. There was a significant improvement in the HA group in all parameters but the difference was greater in the HA+Botox group. No difference was observed in the Botox alone or placebo groups versus baseline.

TABLE 4

Lateral Epicondylitis Subject Characteristics and Outcomes

| Characteristics | Double-blind treatment phase | | | | |
| --- | --- | --- | --- | --- | --- |
| | Baseline (n = 88) | Day 8 (n = 88) | Day 30 (n = 88) | Day 90 (n = 88) | Day 356 (n = 88) |
| VAS Pain on handgrip, Mean (SD) | | | | | |
| HA + Botox | 7.8 (2.2) | −6.7 (2) | −7.8 (1.2) | −7.8 (1.1) | −6.7 (1.3) |
| Botox | 8.1 (2.3) | −2.7 (2) | −3.1 (1.1) | −2.2 (1.1) | −1.1 (0.9) |
| HA | 7.9 (2.3) | −3.10 (1.5)*+ | −3.81 (1.5)*+ | −4.0 (1.8)*+ | −1.27 (0.8)*+ |
| Placebo | 8.2 (2.7) | −1.12 (1.9) | −1.1 (1.72)* | −1.09 (0.8)* | −1.47 (1.0)* |

In the current study, the findings for HA+Botox are unexpected.

In the lateral epicondylitis study, HA+Botox were shown to be superior to any of the other treatment groups. Further, the HA+Botox effect on primary and secondary outcome was greater than the sum of either the HA alone or Botox alone groups. The findings with the Botox alone control group are in keeping with those of some studies previously reported (Wong S M, Hui A C F, Tong P Y, Poon D W F, Yu E, Wong L K S. Treatment of lateral epicondylitis with botulinum toxin. A randomized, double-blind, placebo-controlled trial. Ann Intern Med 2005; 143:793-797) but in disagreement with previous studies that had shown no change (Keizer S B, Rutten H P, Pilot P, Morre H H, van Os J J, Verburg A D. Botulinum toxin injection versus surgical treatment for tennis elbow: a randomized pilot study. Clin Orthop Relat Res 2002; 125-131). Furthermore, the length of follow up was considerably longer than that previously reported in the literature. Specifically, acute improvement in the primary and secondary outcomes was not only found at 8 days, but these findings were persistent up to at least 12 months. Further, the number of subjects studied is greater than that previously reported and adds to the generalizabilty of the results. Small effect sizes and wide confidence intervals previously described may be attributable to small sample sizes.

Dosing, in the lateral epicondylitis study, was similar to those in previous studies (Wong S M, Hui A C F, Tong P Y, Poon D W F, Yu E, Wong L K S. Treatment of lateral epicondylitis with botulinum toxin. A randomized, double-blind, placebo-controlled trial. Ann Intern Med 2005; 143: 793-797; Keizer S B, Rutten H P, Pilot P, Morre H H, van Os J J, Verburg A D. Botulinum toxin injection versus surgical treatment for tennis elbow: a randomized pilot study. Clin Orthop Relat Res 2002; 125-131; Morre H H, Keizer S B, van Os J J. Treatment of chronic tennis elbow with botulinum toxin. Lancet 1997; 349:1746). Landmarks for injection were similar to those previously described using electromyographic guidance (Morre H H, Keizer S B, van Os J J. Treatment of chronic tennis elbow with botulinum toxin. Lancet 1997; 349:1746). Methods were similar to those of Wong et al. (2005) in that the use of the clinical method is more likely to mirror daily practice where electromyography may not be readily feasible (Molloy F M, Shill H A, Kaelin-Lang A, Karp B I. Accuracy of muscle localization without EMG: implications for treatment of limb dystonia. Neurology 2002; 58:806-807). The subjects in the current study included more recent injury as compared to those in previous studies (Wong S M, Hui A C F, Tong P Y, Poon D W F, Yu E, Wong L K S. Treatment of lateral epicondylitis with botulinum toxin. A randomized, double-blind, placebo-controlled trial. Ann Intern Med 2005; 143:793-797; Hayton M J, Santini A J, Hughes P J, Frostick S P, Trail I A, Stanley J K. Botulinum toxin injection in the treatment of tennis elbow. A double-blind, randomized, controlled, pilot study. J Bone Joint Surg Am 2005; 87:503-507).

The results of the current study showed not only positive but unexpectedly superior improvement in lateral epicondylitis with HA and Botox compared to either treatment alone. Further, this novel therapy showed very few adverse effects that were similar to placebo. Faster return to sport with HA+Botox is certainly of importance to those faced with returning to competitive levels of sport earlier in their rehabilitation. Results up to 12 months suggest that the superior improvement with HA+Botox continue to exceed those of other treatments and may impact fewer injuries in the longer term.

In lateral epicondylitis, there are few proven or recommended therapies available. The current findings of enhanced effects greater than either HA or Botox alone with few adverse events are certainly significant in terms of relevance to practice. Further investigation should include those patients presenting with more chronic nature of their disability, including chronic, recurrent tennis elbow.

Although preferred embodiments of the invention have been described herein in detail, it will be understood by those skilled in the art that variations may be made thereto without departing from the spirit of the invention.

What is claimed is:

1. A method for treating sprain or strain injury to a soft tissue selected from the group consisting of epithelial, muscular, and connective tissues in a mammal, the method comprising administering a therapeutically effective amount of hyaluronic acid (HA) and botulinum toxin type A around the site of said soft tissue, wherein administering is done by a mode selected from the group consisting of peri-articular administration, peri-ligamentous administration, peri-musculotendinous administration, peri-fascial administration and combinations thereof, and wherein said HA and botulinum toxin form an internal scaffold around said soft tissue to provide an internal physical support.

2. The method of claim 1, wherein said internal physical support immobilizes the soft tissue.

3. The method of claim 1, wherein said internal physical support restricts further undesired movement of the soft tissue.

4. The method of claim 1, wherein said botulinum toxin paralyzes the soft tissue to help restrict movement of the soft tissue in conjunction with the HA.

5. The method of claim 1, wherein said injured soft tissue is selected from the group consisting of muscle, fascia, tendon and ligament.

6. The method of claim 1, wherein the HA and botulinum toxin is provided as a composition together with a pharmaceutically acceptable carrier.

7. The method of claim 6, wherein the HA has molecular weight of greater than about 500 kDa.

8. The method of claim 7, wherein the HA is provided with a combination of molecular weights.

9. The method of claim 1, wherein HA and botulinum toxin is administered together or concurrently.

10. The method of claim 6, wherein the composition is administered once or repeated several times.

11. The method of claim 1, wherein the administering of the HA and the botulinum toxin is done separately.

12. The method of claim 1, wherein the injured soft tissue is acutely or chronically injured subdermal soft tissue.

13. The method of claim 1, wherein the method is used in conjunction with one or more of an NSAID, a corticosteroid, an inhibitor of cyclooxygenase-2, RICE treatment, rehabilitation, physical treatment, electrical treatment, heat, cold, ultrasound, compression, elevation, immobilization, brace, a plaster cast or a plaster cast.

14. The method of claim 1, wherein said administering is done by peri-articular administration.

15. The method of claim 1, for treating strain injury.

16. The method of claim 1, for treating sprain injury.

17. The method of claim 16, for treating a first degree ankle sprain injury.

18. The method of claim 16, for treating a second degree ankle sprain injury.

19. The method of claim 15, wherein the administering is done within three months of the strain injury.

20. The method of claim 16, wherein the administering is done within 48 hours of the sprain injury.

21. The method of claim 1, wherein the mammal has not received previous local injections to the site of the sprain or strain injury prior to administering the therapeutically effective amount of hyaluronic acid (HA) and botulinum toxin.

* * * * *